United States Patent [19]

Matcham et al.

[11] Patent Number: 5,360,724
[45] Date of Patent: Nov. 1, 1994

[54] PROCESS FOR THE PREPARATION OF CHIRAL 1-ARYL-2-AMINOPROPANES

[75] Inventors: George W. Matcham, Bridgewater; Seujo Lee, Edison, both of N.J.

[73] Assignee: Celgene Corporation, Wayne, N.J.

[21] Appl. No.: 992,575

[22] Filed: Dec. 18, 1992

[51] Int. Cl.$^5$ .............................. C12P 13/00
[52] U.S. Cl. .................. 435/128; 435/193; 435/913; 435/874; 435/832; 435/940; 435/930; 435/921; 435/886; 564/275; 564/375; 564/424
[58] Field of Search ............ 564/424, 272, 375; 435/128; 568/309, 310

[56] References Cited

U.S. PATENT DOCUMENTS 4,000,197  12/1976  Barfknecht ................ 260/570.8
5,169,780  12/1992  Stirling ......................... 435/280

*Primary Examiner*—Glennon H. Hollrah
*Assistant Examiner*—Brian M. Burn
*Attorney, Agent, or Firm*—Mathews, Woodbridge & Collins

[57] ABSTRACT

One chiral form of a 1-aryl-2-aminopropane is produced in preference to its enantiomer by allowing a 1-arylpropan-2-one to react with a 1-amino-1-phenylethane of predominantly one chiral form and reducing the resultant 1-(1-arylprop-2-ylideneimino)-1-phenylethane to yield phenylethane and a mixture of 1-aryl-2-aminopropanes in which one chiral form thereof is present in preference to its enantiomer. The mixture of 1-aryl-2-aminopropanes then is subjected to the action of an omega-amino acid transaminase which converts one of the two chiral forms of 1-aryl-2-aminopropane into the corresponding arylpropanone which can be separated from the remaining chiral form of the 1-aryl-2-aminopropane.

9 Claims, No Drawings

PROCESS FOR THE PREPARATION OF CHIRAL 1-ARYL-2-AMINOPROPANES

The present invention pertains to process for the production of one chiral form of a 1-aryl-2-aminopropane in preference to its enantiomer.

1-Aryl-2-aminopropanes are a recognized class of compounds useful for their own pharmacological properties and as chemical intermediates. 1-Phenyl-2-aminopropanes, also known as phenylisopropyl amines or amphetamines, have been widely studied for their pharmacological action. U.S. Pat. No. 3,689,524 describes a class of compounds inclusive of 1-phenyl-2-aminopropanes which are stated to be cardiovascular agents. U.S. Pat. No. 4,000,197 discloses a range of these compounds having different patterns of aromatic substitution which are utilized in their own right as psychotomimetic agents and as intermediates for the preparation of lysergic acid derivatives.

1-Aryl-2-aminopropanes are chiral, the carbon atom in the 2-position bearing four different substituents: hydrogen; methyl; methyl substituted with an aryl group, e.g., benzyl; and amino. A number of attempts at stereoselective syntheses, that is, a synthesis in which one chiral form is produced preferentially over the other, have been suggested.

Weinges et al., *Chem. Z.*, 94, 728 (1970), reported on a stereospecific synthesis of (S)-1-(3,4-dimethoxyphenyl)-2-aminopropane and (R)-1-(3,4-dimethoxyphenyl)-2-aminopropane in which initial reductive amination of the achiral 1-phenylpropan-2-one with either (R)- or (S)-α-phenethylamine in the presence of hydrogen and Raney nickel under high pressure produced 1-[1-(3,4-dimethoxyphenyl)prop-2-ylamino]1-phenylethane. Hydrogenolysis of this product then yielded (S)-1-(3,4-dimethoxyphenyl)-2-aminopropane or (R)-1-(3,4-dimethoxyphenyl)-2-aminopropane, respectively.

Barfknecht et al., U.S. Pat. No. 4,000,197, reported on an improvement in the Weinges et al. method in which the achiral 1-phenylpropan-2-one is allowed to react with either (R)- or (S)-α-phenethylamine to form an imine (Schiff base) which then is hydrogenated under low pressure to yield 1-(1-phenylprop-2-ylamino)-1-phenylethane. Prior to hydrogenolysis, however, Barfknecht et al. subjected the 1-(1-phenylprop-2-ylamino)-1-phenylethane, which in fact is a diastereoisomeric mixture, to one or more recrystallizations. In the case of (S,S)-1-[1-(3,4-dimethoxyphenyl)prop-2-ylamino]-1-phenylethane, the yield following recrystallization but before hydrogenolysis was reported to be 48% whereas the yield of (S)-1-(3,4-dimethoxyphenyl)-2-aminopropane upon hydrogenolysis was 97%, corresponding to an overall yield of 43%. The enantiomeric purity, (determined by the method of Dale et al., *J. Org. Chem.*, 34, 2543-2549 (1969)) was reported to be 97%. Barfknecht et al. noted that several recrystallizations of the intermediate produced higher enantiomeric purity.

Bloom et al., *J. Med. Chem.*, 35, 3081-3084 (1992) recently described a substituted 1,3-benzodioxole derivative having potent agonistic activity for $\beta_3$ adrenergic receptors. The compound has two chiral centers and was synthesized in a multistep sequence, one step of which involves the reaction of (R)-1-(3,4-dimethoxyphenyl)-2-aminopropane with a chiral epoxide. Pure (R)-1-(3,4-dimethoxyphenyl)-2-aminopropane was synthesized at an overall yield of about 35% through a five step procedure starting with L-DOPA. Analysis using the same method of Dale et al., supra, indicated only the single (R)-isomer was present.

DETAILED DESCRIPTION

The present invention provides an improved method for the synthesis of 1-aryl-2-aminopropanes, in high yield and high chiral purity.

In particular, the present process is suitable for the preparation of the individual enantiomers of compounds of the formula:

in which aryl is an aromatic group of from 6 to 10 carbon atoms which can be unsubstituted or substituted with from 1 to 3 groups.

The aryl group can be varied widely and can be for example phenyl, naphthyl, indyl, tetrahydronaphthyl, and the like. Representative substituents on the aryl group, which when there are more than one can be the same or different group, include hydroxy, halo, alkyl, alkoxy, cyano, amido, carbamoyl, trimethylsilyl, trifluoromethyl, and the like. Since the unsubstituted or substituted aryl group is not involved in the chemical transformations hereafter described, its precise structure is relatively unimportant and perhaps the only structural requirement to be taken into consideration is that any substituent be stable to these chemical transformations, a parameter readily determined by conventional chemical analysis of the product obtained.

Of particular interest due to their pharmacological properties are the subclass of 1-phenyl-2-aminopropanes having the formula:

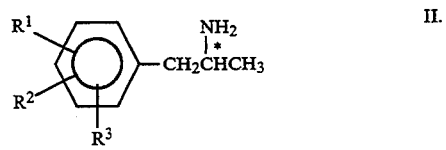

in which each of $R^1$, $R^2$, and $R^3$ independently is hydrogen, hydroxy, halo, trifluoromethyl, alkyl of 1 to 6 carbon atoms, or alkoxy of 1 to 6 carbon atoms.

The term alkyl denotes a univalent saturated branched or straight hydrocarbon chain containing from 1 to 6 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, and isohexyl. Alkoxy refers to alkyl groups bound to the remainder of the molecule through an ethereal oxygen atom. Halogen includes chloro, fluoro, bromo, and iodo.

"Enantiomeric enrichment" as used herein refers to the increase in the amount of one enantiomer as compared to the other. A convenient method of expressing the enantiomeric enrichment achieved is the concept of enantiomer excess, or "ee", which is expressed by the following:

$$ee = \frac{E^1 - E^2}{E^1 + E^2} \times 100$$

in which $E^1$ is the amount of the first chiral form of the amine and $E^2$ is the amount of the second chiral form of the same amine. Thus if the initial ratio of the two chiral forms is 50:50 and an enantiomeric enrichment sufficient to produce a final ratio of 50:30 is achieved, the ee with respect to the first chiral form is 25%, whereas if the final ratio is 70:30, the ee with respect to the first chiral form is 40%.

According to the present process, a 1-arylpropan-2-one is allowed to react with a 1-amino-1-phenylethane of predominantly one chiral form under conditions operable to extract the elements of water and produce the corresponding 1-(1-arylprop-2-ylideneimino)-1-phenylethane. No change in chirality occurs during this initial step. By way of example, a 1-phenylpropan-2-one and a 1-amino-1-phenylethane of predominantly one chiral form simply are heated in a Dean-Stark apparatus to produce the corresponding 1-(1-phenylprop-2-ylideneimino)-1-phenylethane.

The 1-(1-arylprop-2-ylideneimino)-1-phenylethane then is subjected to reduction, as for example catalytically with palladium on carbon, which converts the imine to a secondary amine and generates a new chiral center, and hydrogenolytically removes the phenylethane group, thereby yielding a 1-aryl-2-aminopropane of predominantly one chiral form.

The configuration of the chiral carbon atom in the 1-amino-1-phenylethane starting material will direct the predominant configuration of final product. Hence if (R)-1-amino-1-phenylethane is employed, the principal final product formed from the initial reaction with 1-phenylpropan-2-one will be (R)-1-phenyl-2-aminopropane whereas if (S)-1-amino-1-phenylethane is employed, the principal final product formed from the same 1-arylpropan-2-one will be (S)-1-phenyl-2-aminopropane.

In contrast to the method of Barfknecht et al., supra, the process yields a 1-aryl-2-aminopropane of predominantly one chiral form without the need for intermediate purification and in particular without the need for isolation and recrystallization of the diastereoisomeric intermediate, which complicates large scale processing and inherently reduces the yield.

Optionally the reduction can be performed in two distinct steps. Thus the intermediate 1-(1-arylprop-2-ylideneimino)-1-phenylethane is subjected first to reductive conditions known to reduce the —C=N— bonds of imines, Schiff bases, and hydrazones, as for example lithium aluminum hydride, sodium borohydride, sodium ethoxide, and hydrogen, at relatively low pressure in the presence of a catalyst such as for example Raney nickel to produce a diastereoisomeric mixture of 1-(1-arylprop-2-ylamino)-1-phenylethanes. This diastereoisomeric mixture then is subjected directly to hydrogenolysis, without the need for purification, to produce a mixture of 1-aryl-2-aminopropanes. The hydrogenolysis again can be performed catalytically, as in the presence palladium on carbon, and at elevated pressure.

The enantiomeric mixture of 1-aryl-2-aminopropanes thereby produced typically will have an isomeric range of 80:20 to 95:5; i.e., an ee of 60 to 90%. This mixture of 1-aryl-2-aminopropanes then is subjected to the action of an omega-amino acid transaminase of the type described in U.S. Pat. No. 4,950,606, the disclosure of which is incorporated herein by reference, in an aqueous medium and in the presence of an amino acceptor. The omega-amino acid transaminase is operable to enzymatically convert one chiral form of 1-aryl-2-aminopropane into the corresponding achiral arylpropanone which, if desired, can be recycled.

Omega-amino acid transaminases are known pyridoxal phosphate dependent enzymes found in various microorganisms including Pseudomonas, Escherichia, Bacillus, Saccharomyces, Hansenula, Candida, Streptomyces, Aspergillus, and Neurospora. Two omega-amino acid transaminases which are particularly useful in the present invention, EC 2.6.1.18 and EC 2.6.1.19, have been crystallized and characterized by Yonaha et al., *Agric. Biol. Chem.*, , 47 (10) , 2257–2265 (1983).

The amino acceptor are various carbonyl compounds which are capable of accepting an amino group from an amine under the influence of an omega-amino acid transaminase. These include pyruvate, oxaloacetate, heptaldehyde, glyoxalate, 2-ketobutyrate, butan-2-one, 3-hydroxypyruvate, 2-pentanone, cyclopentanone, and acetophenone.

The enzymatic conversion can be effected by conventional culturing techniques with isolated but non-growing cells, or by bringing the 1-aryl-2-aminopropane into contact with a soluble omega-amino acid transaminase preparation. The omega-amino acid transaminase can be in free form, either as a cell-free extract or a whole cell preparation as noted above, or immobilized on a suitable support or matrix such as cross-linked dextran or agarose, silica, polyamide, or cellulose. It also can be encapsulated in polyacrylamide, alginates, fibers, or the like. Methods for such immobilization are described in the literature (see, for example, *Methods of Enzymology*, 44, 1976). The latter embodiment is particularly useful since once the immobilized enzyme is prepared, one need merely feed the amino acceptor and the mixture of 1-aryl-2-aminopropanes over the immobilized enzyme in order to effect the desired enrichment, and then remove the formed 1-arylpropanone.

The method is suitable for the preparation of either the (R)- or (S)- forms of a wide variety of 1-aryl-2-aminopropanes such as 1-phenyl-2-aminopropane, 1-(4-methoxyphenyl)-2-aminopropane, 1-(2,3-dimethoxyphenyl)-2-aminopropane, 1-(3,4-dimethoxyphenyl)-2-aminopropane, 1-(2,5-dimethoxyphenyl)-2-aminopropane, 1-(2,5-dimethoxy-4-methylphenyl)-2-aminopropane, 1-(2,5-dimethoxy-4-ethylphenyl)-2-aminopropane, 1-(3,4,5-trimethoxyphenyl)-2-aminopropane, and the like.

The following examples will serve to further typify the nature of the invention but should not be construed as a limitation thereof. For the sake of conciseness, these examples demonstrate the process with respect to the preparation of (R)-1-(3,4-dimethoxyphenyl)-2-aminopropane from 1-(3,4-dimethoxyphenyl)propan-2-one and (R)-1-amino-1-phenylethane; the worker need only substitute equivalent amounts of other 1-arylpropan-2-ones for 1-(3,4-dimethoxyphenyl)propan-2-one to produce the corresponding 1-aryl-2-aminopropanes and/or substitute (S)-1-amino-1-phenylethane for (R)-1-amino-1-phenylethane to produce the (S)-enantiomer predominantly.

EXAMPLE 1

1-(3,4-Dimethoxyphenyl)propan-2-one (15.0 g) and (R)-1-amino-1-phenylethane (9.4 g) are mixed with 42.9 mL of toluene and refluxed in a Dean-Stark apparatus for 17 hours to remove water. The reaction mixture then is transferred to a rotary evaporator and the toluene removed. The residual yellow oil contains 1-{1-(3,4-dimethoxyphenyl)prop-2-ylideneimino}-1-phenylethane. This material can be used in the next step without further purification.

EXAMPLE 2

The 1-{1-(3,4-dimethoxyphenyl)prop-2-ylideneimino}-1-phenylethane produced in Example 1 is mixed with 31 mL of ethanol and 6 mL of ethanol-washed Raney-Nickel catalyst. This mixture is placed in a Parr shaker and subjected to hydrogenation at 50 p.s.i. until no further hydrogen uptake occurs (about 24 hours). The Raney-Nickel catalyst then is removed by filtration. The aromatic content of the filtrate contains greater than 92% of 1-{1-(3,4-dimethoxyphenyl)prop-2-ylamino}-1-phenylethane as determined by HPLC (Novapak phenyl column, 0.15% $H_3PO_4$:IPA (70:30), 1.5 mL/mim.). This again can be used in the next step without further purification.

EXAMPLE 3

The ethanolic solution of 1-{1-(3,4-dimethoxyphenyl)prop-2-ylamino}-1-phenylethane is mixed with 4 mL of glacial acetic acid and 1.25 g of 10% Pd/C is added. This mixture is subjected to hydrogenation in a Parr shaker at 50 p.s.i. and 50° C. until no further hydrogen uptake occurs (about 4 to 5 hours). After removal of the catalyst by filtration, ethanol is removed by rotary evaporation to leave a solid. The solid is dissolved in 100 mL of distilled water, the pH adjusted to 4.0 with concentrated hydrochloric acid and extracted twice with xylene. The the pH of the aqueous solution then is raised to 13 with sodium hydroxide. The free amine is extracted twice with 100 mL portions of xylene, and recovered by rotary evaporation to remove the solvent. The oily residue is distilled under vacuum and 10.85 g of (R)-1-(3,4-dimethoxyphenyl)-2-aminopropane (72%) are collected 146°-151° C./1.5 mm Hg. The ee is determined to be 90.3%.

EXAMPLE 4

A reaction mixture of 185 mL is prepared containing 10.85 g (R)-1-(3,4-dimethoxyphenyl)-2-aminopropane (0.3M), sodium pyruvate (0.033M); pyridoxal phosphate (0.6 mM), and 310 units of omega amino acid transaminase from *Bacillus megaterium* as described in U.S. Pat. No. 4,950,606. The pH is adjusted to 7.0 with hydrochloric acid. After incubation for 16 hours at 35° C., the pH is adjusted to 4.0 and 3,4-dimethoxyphenylpropanone is removed by extraction (2×) into 185 mL of xylene. The pH of the aqueous solution then is raised to 13 with 50% sodium hydroxide and extracted twice with 185 mL portions of xylene. After removal of the xylene by rotary extraction, 9.4 g of (R)-1-(3,4-dimethoxy)phenyl-2-aminopropane are recovered from as a clear liquid by distillation under vacuum at 146°-151° C./1.5 mm Hg. This analyzes at greater than 98% chemical purity and has an ee greater than 99%.

EXAMPLE 5

1-{1-(3,4-Dimethoxyphenyl)prop-2-ylideneimino}-1-phenylethane, produced from 50 g of 1-(3,4-dimethoxyphenyl)propan-2-one and 30 g of (R)-1-amino-1-phenylethane according to the procedure of Example 1, in 62.5 mL of ethanol is hydrogenated in a Parr apparatus in the presence of 10% Pd/C at 50 p.s.i. and 20° C. When there is no further uptake of hydrogen (about 16 hours), the catalyst is removed by filtration and the residual ethanol and phenylethane are removed by evaporation to yield 43.2 g of (R)-1-(3,4-dimethoxy)-phenyl-2-aminopropane which is distilled at 146°-151° C./1.5 mm Hg. The product, which had an ee of 60%, then is subjected to the action of an omega amino acid transaminase from *Bacillus megaterium* as already described supra in Example 4 to produce (R)-1-(3,4-dimethoxy)phenyl-2-aminopropane having an ee greater than 99%.

What is claimed is:

1. The process of producing one chiral form of a 1-phenyl-2-aminopropane in preference to its enantiomer which comprises:
   (i) allowing a 1-phenylpropan-2-one to react with a 1-amino-1-phenylethane of predominantly one chiral form to produce the corresponding 1-(1-phenylprop-2-ylideneimino)-1-phenylethane;
   (ii) reducing the resultant 1-(1-phenylprop-2-ylideneimino)-1-phenylethane to yield phenylethane and a mixture of 1-phenyl-2-aminopropanes in which one chiral form thereof is present in preference to its enantiomer; and
   (iii) subjecting the mixture of 1-phenyl-2-aminopropanes, in an aqueous medium and in the presence of an amino acceptor, to the action of an omega-amino acid transaminase operable to enzymatically convert one chiral form of 1-phenyl-2-aminopropane into the corresponding 1-phenylpropanone and thereby increase the relative proportion of the chiral form of the 1-phenyl-2-aminopropane which is not enzymatically converted.

2. The process according to claim 1 wherein said 1-phenyl-2-aminopropane-2-one is of the formula:

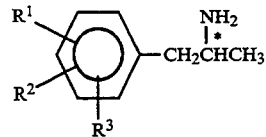

in which each of $R^1$, $R^2$, and $R^3$ independently is hydrogen, hydroxy, halo, trifluoromethyl, alkyl of 1 to 6 carbon atoms, or alkoxy of 1 to 6 carbon atoms.

3. The process according to claim 2 in which each of $R^1$ and $R^2$ independently is hydrogen or alkoxy of 1 to 6 carbon atoms and $R^3$ is hydrogen.

4. The process according to claim 1 wherein said 1-phenylpropan-2-one is 1-(3,4-dimethoxyphenyl)propan-2-one and said 1-phenyl-2-aminopropane is (R)-1-(3,4-dimethoxyphenyl)-2-aminopropane.

5. The process according to claim 1 wherein 1-(1-phenylprop-2-ylideneimino)-1-phenylethane is first reduced to form a diastereoisomeric mixture of the corresponding 1-(1-phenylprop-2-ylamino)-1-phenylethanes and the diastereoisomeric mixture of the 1-(1-phenylprop-2-ylamino)-1-phenylethanes then is subjected to hydrogenolysis to yield phenylethane and a mixture of 1-phenyl-2-aminopropanes in which one chiral form thereof is present in preference to its enantiomer.

6. The process according to claim 5 wherein said 1-phenyl-2-aminopropane is of the formula:

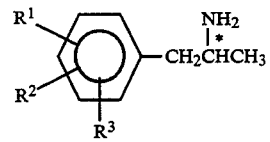

in which each of $R^1$, $R^2$, and $R^3$ independently is hydrogen, hydroxy, halo, trifluoromethyl, alkyl of 1 to 6 carbon atoms, or alkoxy of 1 to 6 carbon atoms.

7. The process according to claim 6 in which each of $R^1$ and $R^2$ independently is hydrogen or alkoxy of 1 to 6 carbon atoms and $R^3$ is hydrogen.

8. The process according to claim 5 wherein said 1-phenylpropan-2-one is 1-(3,4-dimethoxyphenyl)propan-2-one and said 1-phenyl-2-aminopropane is (R)-1-(3,4-dimethoxyphenyl)-2-aminopropane.

9. The process of producing one chiral form of a 1-phenyl-2-aminopropane in preference to its enantiomer which comprises:
(i) allowing a 1-phenylpropan-2-one to react with a 1-amino-1-phenylethane of predominantly one chiral form to form a corresponding 1-(1-phenylprop-2-ylideneimino)-1-phenylethane of predominantly one chiral form;
(ii) reducing the resultant 1-(1-phenylprop-2-ylideneimino)-1-phenylethane to form a diastereoisomeric mixture of the corresponding 1-(1-phenylprop-2-ylamino)-1-phenylethanes;
(iii) subjecting the diastereoisomeric mixture of the 1-(1-phenylprop-2-ylamino)-1-phenylethanes, without further enantiomeric enrichment, to hydrogenolysis to yield a mixture of 1-phenyl-2-aminopropanes in which one chiral form thereof is formed in preference to its enantiomer and 1-amino-1-phenylethane; and
(iv) subjecting the mixture of 1-phenyl-2-aminopropanes, in an aqueous medium and in the presence of an amino acceptor, to the action of an omega-amino acid transaminase operable to enzymatically convert one chiral form of 1-phenyl-2-aminopropane into the corresponding 1-phenylpropanone and thereby increase the relative proportion of the chiral form of the 1-phenyl-2-aminopropane which is not enzymatically converted.

* * * * *